United States Patent [19]
Zepp

[11] Patent Number: 5,605,616
[45] Date of Patent: Feb. 25, 1997

[54] REVERSIBLE CHARGE-BASED SEQUESTRATION ON SOLID SUPPORT

[75] Inventor: Charles M. Zepp, Hardwick, Mass.

[73] Assignee: VersiCor, Inc., Marlborough, Mass.

[21] Appl. No.: 553,842

[22] Filed: Nov. 6, 1995

[51] Int. Cl.$^6$ ..................................................... C25F 5/00
[52] U.S. Cl. ........................... 205/688; 205/710; 205/766
[58] Field of Search ........................ 204/157.15, 158.21, 204/451; 205/688, 687, 704, 710, 766

[56] References Cited

U.S. PATENT DOCUMENTS

| | | | |
|---|---|---|---|
| 4,585,652 | 4/1986 | Miller et al. | 205/688 |
| 4,629,544 | 12/1986 | Bonaventura et al. | 204/131 |
| 4,803,170 | 2/1989 | Stanton et al. | 436/518 |
| 5,208,154 | 5/1993 | Weaver et al. | 435/176 |
| 5,284,558 | 2/1994 | Linhardt et al. | 205/451 |
| 5,439,829 | 8/1995 | Anderson et al. | 436/518 |
| 5,453,186 | 9/1995 | Müller et al. | 210/198 |
| 5,453,199 | 9/1995 | Afeyan et al. | 210/638 |

FOREIGN PATENT DOCUMENTS

94/08051  4/1994  WIPO .

OTHER PUBLICATIONS

Gordon et al., "Applications of Combinatorial Technologies to Drug Discovery. 2. Combinatorial Organic Synthesis, Library Screening Strategies, and Future Directions," *Journal of Medicinal Chemistry*, vol. 37, No. 10, May 13, 1994.

Hobbs DeWitt et al., "Diversomers: An approach to non-peptide, nonoligomeric chemical diversity," *Proc. Natl. Acad. Sci. USA*, vol. 90, Aug. 1993, pp. 6909–6913.

Houghten et al., "Generation and use of synthetic peptide combinatorial libraries for basic research and drug discovery," *Nature*, vol. 354, Nov. 1991, pp. 84–86.

*Primary Examiner*—Kathryn Gorgos
*Assistant Examiner*—Edna Wong
*Attorney, Agent, or Firm*—Lahive & Cockfield; Matthew P. Vincent; Giulio A. DeConti, Jr.

[57] ABSTRACT

Methods for reversibly associating a substrate compound and a solid support are described. In general, the methods feature the use of selectively chargeable moieties. Apparatus for use with the methods of the invention is also described.

23 Claims, 1 Drawing Sheet

FIG. 1

REVERSIBLE CHARGE-BASED SEQUESTRATION ON SOLID SUPPORT

BACKGROUND OF THE INVENTION

The increasing need for methods of synthesizing complex chemical compounds has led, in recent years, to the development of new techniques for synthesizing, and subsequently screening, large numbers of compounds. In general, a highly desirable feature of any new method of synthesis is that the purification of intermediates, and preferably of the final products, be rapid and inexpensive. Crystallization is commonly employed, but not all compounds can be readily crystallized. Chromatographic separation, as required by some older methods, is prohibitively expensive and time-consuming, particularly when performed on large quantities of compounds, or when many impurities are present.

For this reason, synthetic methods that employ solid-phase supports for synthesis of complex molecules have become increasingly popular. The ability to easily handle and purify polymer-supported materials has facilitated the development of combinatorial approaches to pharmaceutical synthesis and screening, and has resulted in a dramatic increase in the number of drug candidates that can be developed and tested in a relatively short period of time.

Solid-phase reactions have certain disadvantages, however, compared to reactions in solution. One disadvantage is the inability to use reactants which are not soluble in the reaction medium (for example, certain catalysts). Another frequent disadvantage is the need to use solvents which are capable of swelling the polymer support. The efficiency and selectivity of a reaction carried out on a solid phase can vary greatly relative to the reaction in solution. For example, yields can be affected, reaction times lengthened, and selectivity (e.g., enantioselectivity or regioselectivity) of a reaction on a solid support can be different from the corresponding solution-phase reaction. Furthermore, the need to ensure complete reaction throughout the heterogeneous reaction mixture can lead to longer reaction times than are required in solution-phase chemistry.

SUMMARY OF THE INVENTION

In one aspect, the invention provides a method for modifying a substrate compound. The method comprises providing, in a reaction mixture, a substrate compound comprising a reactive moiety; contacting the reactive moiety with a reactant to form a modified substrate compound; providing a solid support, wherein one of said substrate compound and said solid support comprises a selectively chargeable moiety (SCM) having a non-associating charge state; altering the non-associating charge state of the selectively chargeable moiety to an associating charge state; contacting the modified substrate compound with the solid support such that the modified substrate compound is sequestered by the solid support; and altering the associating charge state of the selectively chargeable moiety to a non-associating charge state such that the modified substrate compound is not sequestered by the solid support. In preferred embodiments, the substrate compound comprises a selectively chargeable moiety. In preferred embodiments, the solid support comprises a selectively chargeable moiety. In preferred embodiments, at least one of an oxidizing or reducing step for reversibly oxidizing the SCM comprises a chemical redox reaction, an electrochemical redox reaction, or a photochemical redox reaction. In preferred embodiments, the solid support is insoluble In preferred embodiments, the solid support comprises an electrode including an adsorbent which associates with an SCM in the associating charge state and associates less with an SCM in the non-associating charge state. In preferred embodiments, the solid support is selectively chargeable. In preferred embodiments, the SCM comprises a reversibly oxidizable dye group. In more preferred embodiments, the dye is a cationic dye or an anionic dye. In preferred embodiments, the dye is selected from the group consisting of xanthenes, acridines, phenazines, azines, oxazines, thiazines, cyanines, methines, polymethines, viologens, quinones, diphenylmethanes, triarylmethanes, and azuleniums. In preferred embodiments, the compound containing the SCM has a molecular weight less than about 5000 a.m.u.; the compound containing the SCM is insoluble in aqueous solution.

In another aspect, the invention provides a method for reversibly associating a compound with a solid support. The method comprises providing, in a reaction mixture, a compound including a selectively chargeable moiety (SCM) which can be reversibly oxidized between an associating charge state which can associate with the solid support and a non-associating charge state which associates less with the solid support; contacting the reaction mixture containing the compound with a solid support under conditions that the SCM is in the associating charge state and the compound associates with the solid support; separating the solid support from at least a portion of the mixture; and altering the charge state of the SCM to a non-associating charge state such that the compound dissociates from the solid support.

In another aspect, the invention provides a method for modifying a substrate compound. The method comprises providing, in a reaction mixture, a substrate compound comprising a selectively chargeable moiety having a non-associating charge state, and a reactive moiety; contacting the reactive moiety with a reactant to form a modified substrate compound; altering, by an electrochemical redox reaction, the non-associating charge state of the selectively chargeable moiety to an associating charge state; contacting the selectively chargeable moiety with a solid support such that the modified substrate compound is sequestered by the solid support; separating the solid support from the at least a portion of the mixture; and altering, by an electrochemical redox reaction, the associating charge state of the selectively chargeable moiety to a non-associating charge state such that the modified substrate compound is not sequestered by the solid support.

In yet another aspect, the invention provides a method for reversibly sequestering a substrate compound on a solid support. The method comprises providing, in a reaction mixture, a substrate compound comprising a selectively chargeable moiety capable of altering oxidation states; reacting the substrate compound with a reactant; contacting the reaction mixture with a means for altering an oxidation state of the chargeable moiety from a state which does not bind to the solid support to a state which does bind to the solid support; contacting the substrate compound with the solid support such that the substrate compound becomes sequestered by the support; disposing the support in a second reaction mixture; contacting the reaction mixture with a means for altering an oxidation state of the chargeable moiety from a state which does bind to the solid support to a state which does not bind to the solid support; such that the substrate compound is not sequestered by the support. In preferred embodiments, the method further comprises, after the step of contacting the substrate compound with the solid support, the step of washing the solid support.

Yet another aspect of the present invention relates to an apparatus for providing reversible solid phase sequestration of solution phase reaction components. In general, the apparatus can be characterized as including, (i) one or more reaction vessels for containing a solution phase reaction mixture having a substrate compound including a chargeable moiety; (ii) one or more reagent vessels; (iii) a delivery system for delivering reagents from the reagent vessels to the reaction vessels; (iv) solid support means for reversibly sequestering the chargeable moiety from the reaction mixture in an oxidation-dependent manner; and (v) redox means for reversibly oxidizing and reducing the chargeable moiety between a charge state which associates with the solid support means and a charge state which does not readily associate with the solid support means. In preferred embodiments, a microprocessor is included for coordinating operation of one or more of the delivery system, solid support means and redox means.

The subject apparatus is specifically contemplated for use in combinatorial synthetic schemes which utilize the reversible sequestration reaction of the present invention. Accordingly, the apparatus includes a plurality of the reaction vessels and reagent vessels for simultaneously providing two or more different reaction mixtures.

DETAILED DESCRIPTION OF THE INVENTION

Recent advances in reactions of compounds immobilized on solid phase supports have led to new approaches to chemical synthesis and screening. One significant advantage of solid-phase synthesis (SPS) is the ease with which products can be separated and purified. Simple filtration of the solid support (for example, resin beads), and washing to remove impurities, is often the only purification required.

The present invention provides a novel technique for reversibly sequestering a compound on a solid support. In the methods of the invention, a substrate compound can undergo reaction in liquid reaction phase, and the resulting product removed from the mixture (and from impurities) by temporary (e.g., reversible) association with a soluble support. The sequestered compound, on the solid support, can then be rapidly purified, and the purified compound returned to a reaction mixture by dissociation from the solid support.

This technique is useful for synthetic reactions, particularly multi-step synthesis schemes. For instance, the invention provides a method for making synthetic products by reversibly sequestering a substrate compound on a solid support. This method involves providing, in a reaction mixture, a substrate compound which includes a reactive moiety and a selectively chargeable moiety capable of altering oxidation states, and reacting the reactive moiety of the substrate compound with a reactant. When reaction is complete, the reaction mixture is contacted with a means for altering an oxidation state of the chargeable moiety from a state which does not bind to a solid support to a state which does bind to a solid support, and the substrate compound is then contacted with the solid support such that the substrate compound becomes sequestered by the support. The solid support is then disposed in a second reaction mixture, and the reaction mixture is contacted with a means for altering an oxidation state of the chargeable moiety from a state which does bind to the solid support to a state which does not bind to the solid support, such the said substrate compound is not sequestered by, and is dissociated from, the support. Cleavage of the synthetic product from the substrate compound yields the desired product.

Definitions

For convenience, certain terms used in the specification, examples, and appended claims are collected here.

The term "substrate compound", as used herein, refers to a chemical compound that comprises at least one of a selectively chargeable moiety or a charged moiety. In preferred embodiments, a substrate compound comprises at least one selectively chargeable moiety. The substrate compound can also include one or more reactive moieties, as well as linkers, spacers, and other unreactive moieties. In preferred embodiments, the substrate compound can be represented by the general formula A-B, wherein A represents a selectively chargeable moiety able to undergo a redox-reversible change in charge state and B represents a reactive moiety for a chemical reaction, which is generally a reaction other than a redox reaction of A, A and B being discrete portions of the compound from one another.

The term "sequester", as used herein, means to separate, segregate, remove, or bind a substrate compound, e.g., on a solid support. In preferred embodiments, a compound is sequestered by a solid support such that other non-sequestered compounds can be removed, e.g., by washing or other purification techniques. A compound is "reversibly sequestered" if the process of sequestering the compound on a solid support can be reversed to yield a free compound, e.g., in solution in a reaction mixture. In preferred embodiments, the process of sequestering a compound, or of reversing the sequestration, or both, occurs under mild conditions and in high yield, e.g., greater than at least about 40% yield.

The term "chargeable moiety", as used herein, refers to a chemical moiety that is capable of being converted, by oxidation or reduction, to a charged state or condition. In preferred embodiments, a chargeable moiety is capable of assuming at least two charge states. Thus, a "selectively chargeable moiety" is a moiety that can assume at least two charge states, as defined below, and the charge state of the moiety can be selected, controlled, or altered, e.g., by the methods described infra. In preferred embodiments, a chargeable moiety is selectively chargeable.

The term "solid support", as used herein, refers to a support phase or surface which is not soluble in a reaction mixture or forms a two-phase system with a reaction mixture. Although a solid phase support is preferred, other phases such as hydrogels are also useful in the methods of the invention.

The term "associating", as used herein, means being able to associate with, or bind to, a solid support. The association is preferably non-covalent, e.g., ionic, although other interactions are possible. In general, the strength of association or binding will be sufficient to allow isolation of a solid support and a compound associated therewith. In preferred embodiments, association is primarily mediated by non-covalent interactions other than van der Waals forces or hydrogen bonds. The term "non-associating", as used herein, means not capable of associating, as defined above.

The term "charge state", as used herein, refers to the overall electric charge of a subject moiety or compound. In general, charge states fall into three categories: uncharged (electrically neutral), negatively charged (anionic), or positively charged (cationic). Examples of preferred charge states include +2, +1 (cationic); 0 (uncharged); −1 and −2 (anionic). More preferred charge states include +1, 0, and −1. Particularly preferred pairs of charge states are 0, +1 and 0, −1, i.e., in preferred embodiments, a selectively chargeable moiety can be reversibly cycled between charge states 0 and +1, or between 0 and −1. In preferred embodiments, a subject compound is "non-associating" when it has a charge state of 0.

A compound or moiety that can be "reversibly cycled", as used herein, refers to a compound that is capable of undergoing a reversible cycle between at least two different charge states. Cycling can be achieved by the methods described herein, e.g., reversible oxidation or adduct formation. A compound or moiety that can be "reversibly oxidized", as used herein, refers to a compound that is capable of undergoing a reversible redox reaction. For example, a compound that is oxidized from a reduced form to an oxidized form, and then converted (by reduction) to a reduced form, is said to be "reversibly oxidized", as is a compound that can be reduced from an oxidized form to a reduced form, followed by oxidation to an oxidized form.

The terms "oxidant" or "oxidizing agent" are known in the art and, as used herein, refer to an agent or reaction condition that can accept, or cause the loss of, one or more electrons from a chargeable moiety. Similarly, the terms "reductant" or "reducing agent", as used herein, refer to an agent or reaction condition that can donate, or cause the gain of, one or more electrons to a chargeable moiety. The terms "oxidizing agent" and "reducing agent" are further intended to embrace electrochemical conditions for oxidation and reduction, respectively.

The term "reactive moiety", as used herein, refers to a chemical moiety of a substrate compound that can react with a reagent to form a modified, e.g., different, chemical moiety. The modified chemical moiety so produced is also referred to herein as a reactive moiety or a "synthetic product". In preferred embodiments, a reactive moiety is not functionally a part of the chargeable moiety. For example, a reactive moiety can react with nucleophiles, electrophiles, free radicals, redox reagents, and the like. In preferred embodiments, a reactive moiety is selected to react with a reagent under conditions such that other moieties of the substrate compound (e.g., selectively chargeable moieties, linkers, spacers, and the like) are not reactive. In preferred embodiments, a reactive moiety is selected to be unreactive under conditions where a "chargeable moiety" is converted from one charge state to another charge state.

The term "synthetic product", as used herein, refers to a product which is synthesized according to the methods of the invention. A "synthetic product" can be joined or linked to a substrate compound, or it can be cleaved from the substrate compound, as described below.

Chargeable moieties

As described above, a chargeable moiety suitable for use in the present invention should have at least one or more of the following properties: 1) it should be able to assume at least two charge states; 2) a chargeable moiety, and the substrate compound of which it is part, should be stable in at least two charge states, e.g., in a useful charge state, little or no decomposition of the substrate compound should occur; 3) it should be possible to select and access at least two charge states under conditions compatible with stability of the substrate compound; 4) conversion from one charge state to another charge state should be by oxidation or reduction; and 5) at least one associating and one non-associating charge state should be accessible. Furthermore, in preferred embodiments, the process of altering a first charge state to obtain a second charge state is reversible, e.g., the second charge state can then be altered back to the first charge state.

Chargeable moieties suitable for use in the present invention include a variety of moieties known in the art which undergo reversible redox reactions. Exemplary chargeable moieties include heterocyclic compounds such as nicotinic acid derivatives, flavins (e.g., flavin mononucleotide (FMN)), phenazinium compounds, and pyridinium compounds. Another class of preferred chargeable moieties includes both anionic and cationic dyes. Examples of useful dyes include xanthenes, acridines, phenazines, azines, oxazines, thiazines, cyanines, methines, polymethines, viologens, quinones, diphenylmethanes, triarylmethanes, azuleniums, and the like.

In general, where the charge state of the polymer support is cationic, a dye selected for use as a chargeable moiety can be an anionic dye. Likewise, where the solid support is anionic, a cationic dye will preferred, such as, e.g., victoria blue, methylene blue, crystal violet, methyl violet, rhodamine red, Auramine yellow, acridine orange, auramine O, pyronine Y, thioflavin T, Brilliant Green G, Brilliant Blue R, Lissamine Green B, Patent Blue VF, and propidium iodide.

Certain dyes can have the additional advantage of providing a visual indication of the completeness of reaction because they generally are colored in only one of two charge states. For example, triarylmethane dyes are colored in the cationic (oxidized) state, but are colorless in the neutral (reduced) state. Thus, for triarylmethane dyes, absence or disappearance of color indicates complete conversion to the reduced state.

In preferred embodiments, the charge state of a substrate compound is altered in a redox reaction. As used herein, the term "redox reaction" means a transfer of electrons to or from a substrate compound, but preferably does not include proton transfers (although hydride transfer is considered a redox reaction for purposes of the invention). Thus, in preferred embodiments, the charge state of a substrate compound can be altered by reactions other than proton transfer (protonation or deprotonation).

Preferred chargeable moieties can assume an uncharged state. For example, a triarylmethane dye such as Malachite Green can assume both a cationic (charged) state and a neutral, uncharged state. Thus, certain preferred chargeable moieties can assume charge states of +1 and a charge state of 0. Other preferred chargeable moieties can assume charge states of −1 and 0. In certain embodiments, however, a chargeable compound can assume more than one cationic state (e.g., +1 and +2); more than one anionic state (e.g., −1 and −2); or one cationic and one anionic state (e.g., +1 and −1). In other preferred embodiments, the chargeable moiety can assume a state which results in an uncharged substrate compound as a whole. For example, a substrate compound having a chargeable moiety with a charge of −1, and a reactive moiety (or linking moiety) with a charge of +1, can have an overall charge state of 0 (neutral).

In other embodiments, a chargeable moiety can assume at least two charge states which do not include an electrically neutral state. For example, a chargeable moiety that can assume a charge of +1 and a charge of −1, but not a charge of 0, is useful in certain embodiments of the invention.

In a further embodiment, a substrate compound includes more than one chargeable moiety. In this embodiment, the chargeable moieties can be all the same or can be different. By selection of a suitable number and type(s) of chargeable moiety, the overall electrical charge of the substrate compound, and the conditions under which the overall charge can be altered, can be controlled. Moreover, by selectively charging individual chargeable moieties, the overall charge state of the substrate compound can be determined by any permissible combination of charges on the chargeable moieties.

In selecting a chargeable moiety, the skilled artisan will consider the redox potential of the chargeable moiety and other moieties, if any, of the substrate molecule, both to ensure that the chargeable moiety can be oxidized and reduced under experimentally accessible conditions, and to avoid interfering redox reactions of other moieties of the substrate molecule (e.g., a reactive moiety). For example, the redox potential of a chargeable moiety should be in a range available from, e.g., use of chemical reagents or electrochemical equipment, and should not be in a range that will cause undesired oxidation or reduction of other moieties.

In selecting a chargeable moiety, the skilled artisan will also consider the relative affinity of the chargeable moiety, and the substrate compound as a whole, for the solid support. Relative affinities can be determined by techniques such as chromatography, or by the method described in Example 4, infra. Thus, in preferred embodiments, a chargeable moiety in a non-associating charge state will have relatively little affinity for the solid support as compared with the affinity for the solid support of the chargeable moiety in an associating charge state. Thus, in preferred embodiments, the affinity of a given solid support for a chargeable moiety or substrate compound in an associating charge state will be at least 1.5, 2, 3, 5, 10 or 20 times greater than the affinity of that solid support for the same chargeable moiety or substrate compound in a non-associating charge state.

Substrate compounds

A substrate compound suitable for use in the invention can be selected by the skilled artisan. In general, a suitable substrate compound comprises at least one chargeable moiety. In preferred embodiments, the substrate compound further includes at least one reactive moiety. In particularly preferred embodiments, as described in more detail below, the substrate compound includes more than one reactive moiety.

A substrate compound will, in certain embodiments, be chosen to have suitable chargeable and reactive functionalities for the synthesis of a desired synthetic product.

Methods of altering charge state

As discussed above, the charge state of a chargeable moiety (and thus of the substrate compound) can be selected or altered by oxidation or reduction, i.e., redox reaction. Methods known in the art for oxidation or reduction of compounds can be employed to alter the charge state of a chargeable moiety. Methods of oxidation or reduction can be selected by the skilled artisan according to several criteria. In general, a suitable oxidation or reduction method (a "redox" method) will have one or more of the following properties: 1) It will be capable of reacting with the chargeable moiety; 2) It will alter the charge state of the chargeable moiety; and 3) It will not substantially react with the substrate compound at functionalities other than the chargeable moiety, unless reaction at such other functionality is desired. In preferred embodiments, an oxidation or reduction method is selected such that a chargeable moiety is oxidized or reduced without affecting other functionalities present in the substrate compound. While undesirable side reactions (such as reactions with other functionalities) may occur, the rates of such reactions can be manipulated through the selection of reactants and conditions to be slow in comparison to the desired reaction(s).

For example, in one embodiment, the chargeable moiety is oxidized or reduced by a chemical reagent. A variety of oxidizing and reducing agents are known in the art (see, e.g., M. Hudlicky, "Oxidations in Organic Chemistry", American Chemical Society, (1990)), and illustratively include the following:

Oxidizing agents: DDQ, $Pb(OAc)_4$, $Tl(NO_3)_3$, o- or p-chloranil, $O_2$, $MnO_2$, $SeO_2$, $Hg(OAc)_2$, $RuO_4$, $Br_2$, NaOCl, $KMnO_4$, $NaIO_4$, $K_2Cr_2O_7$, $K_3Fe(CN)_6$, $Ag_2O$, ozone, $I_2$, $FeCl_3$, ceric ammonium nitrate, trityl tetrafluoroborate, and the like.

Reducing agents: $NaBH_4$, $NaCNBH_4$, $BH_3$, $LiAlH_4$, $Li/NH_3$, $Na/NH_3$, $H_2$, Zn, Raney nickel, $SnCl_2$, triethylsilane, lithium aluminum hydride, and the like.

Chemical oxidants and reductants vary in specificity for particular functionalities. Also, combinations of oxidants, or catalysts, initiators, or promoters for use with stoichiometric oxidants, may be advantageous in certain cases. For example, oxidation by the oxidant $^1O_2$ can be initiated by light, in the presence of a suitable photoinitiator, which can be a moiety of a substrate compound, or can be a separately added compound. The choice of an oxidant or reductant to alter the charge of the chargeable moiety, without causing interfering reactions with other functionalities, will be routine to the skilled artisan.

In another embodiment, the chargeable moiety is oxidized or reduced by an electrochemical reaction. In this embodiment, a source of electric current, e.g., an electrode, can be employed to provide electric current of a selected potential sufficient to cause oxidation or reduction of a chargeable moiety. Equipment for electrochemical reactions is commercially available and has been described (see, e.g., A. J. Fry, "Synthetic Organic Electrochemistry", John Wiley & Sons New York (1989) and references cited therein). The selectivity of electrochemical reactions can, in general, be adjusted by tuning the potential of the current. Furthermore, certain reactions can be reversed by simply manipulating the polarity and potential of the current; this has the advantage of experimental simplicity. In certain embodiments, a charge carrier such as an electrolyte can be added to facilitate electrochemical reactions.

In yet another embodiment, the chargeable moiety is oxidized or reduced by electromagnetic radiation. For example, light-initiated redox reactions are known in which an uncharged moiety becomes charged upon irradiation with light of a suitable wavelength. An illustrative photochemical reaction is shown below (Scheme 1):

Scheme 1

Scheme 1

Scheme 2

In Scheme 1, absorption of light of an appropriate wavelength results in internal redox reaction to yield a charged moiety, with an overall change in charge state from 0 to +1. Although certain photochemical reactions are not reversible by photochemical means, other means of reversing the reaction (e.g., chemical or electrochemical means) can be employed. In preferred embodiments, the light used for photochemical reaction is ultraviolet light. In other preferred embodiments, the light is visible light. In yet other embodiments, electromagnetic radiation in the gamma or X-ray range is employed for oxidation or reduction.

In certain embodiments, a chargeable moiety is oxidized or reduced by a combination of chemical, electrochemical, and photochemical reactions. For example, a chargeable moiety can be reduced by a chemical reducing agent, and subsequently oxidized by an electrochemical reaction. In other embodiments, when it is desired to oxidize or reduce a chargeable moiety by more than one electron, the oxidation or reduction can take place in several steps. For example, when a two-electron oxidation of a chargeable moiety is desired, a one-electron electrochemical oxidation can be followed by a further one-electron oxidation chemical with a chemical agent, to achieve the desired two-electron oxidation. The skilled artisan will be able to select a condition or set of conditions to achieve the desired reversible oxidation or reduction.

It will be appreciated that redox chemistry provides a convenient means for altering the charge state of a substrate compound. Many redox reactions can be performed under a wide variety of reaction conditions and are compatible with many common chemical functionalities. Thus, in preferred embodiments, the charge state of a substrate compound or moiety is altered by redox reaction(s).

In a further embodiment, the charge state of a substrate compound can be altered by reversible adduct formation. For example, a cationic triarylmethane dye can react, when treated with a nucleophile, to yield a neutral adduct. For example, the reaction of a triarylmethane dye with the nucleophile thiophenol is shown in Scheme 2.

In this reaction, the cationic substrate compound is converted to the neutral adduct. Such reactions can be effected by addition of a suitable nucleophile, or, in certain cases, by adjusting the pH to generate the hydroxide nucleophile. In preferred embodiments, reversible adduct formation does not embrace protonation or deprotonation reactions of the substrate compound.

Reactive moieties

In another aspect of the invention, the substrate compound further includes a reactive moiety. In general, a reactive moiety is selected to undergo a desired reaction and to be unreactive under redox conditions employed to alter the charge state of the chargeable moiety. However, in certain embodiments, a reactive moiety is reactive under the redox conditions, for example, when it is desired to oxidize or reduce the reactive moiety.

In preferred embodiments, the reactive moiety is not functionally a part of the chargeable moiety, that is, reaction at the reactive moiety does not significantly alter the properties of the chargeable moiety. A reactive moiety can react with nucleophiles, electrophiles, free radicals, redox reagents, and the like. In preferred embodiments, a reactive moiety is selected to react with a reagent under conditions such that other moieties of the substrate compound (e.g., selectively chargeable moieties, linkers, spacers, and the like) are not reactive. In other preferred embodiments, a reactive moiety is selected to be unreactive under conditions where a "chargeable moiety" is converted from one charge state to another charge state.

A reactive moiety can be linked or joined to a chargeable moiety by methods known in the art. In certain embodiments, linking or spacer moieties can be employed in joining the reactive moiety to the chargeable moiety. In preferred embodiments, the reactive moiety is joined to a chargeable moiety through a cleavable linkage, e.g., a linkage that can be cleaved to release the reactive moiety from the chargeable moiety. For example, a reactive moiety can be joined to a chargeable moiety through an ester moiety. Cleavage of the ester moiety releases the reactive moiety (or the synthetic product) from the chargeable moiety.

In certain preferred embodiments, a substrate compound can include more than one reactive moiety. A substrate compound that comprises more than one reactive moiety thus has more than one reactive site. For example, the dendrimer substrate compound of Example 7, infra, comprises twelve reactive moieties (hydroxyl groups) which can be used for synthesis of synthetic products. This embodiment advantageously provides a substrate compound with a high capacity for synthetic products, e.g., the dendrimer compound cited above has twelve times the capacity of a substrate compound that has only one reactive moiety.

In general, the reactive moieties will be selected to be the same, but in certain embodiments, the reactive moieties may be different. The use of different reactive moieties allows the synthesis of multiple synthetic products on a single substrate compound.

Synthetic products

The methods of the invention can be employed to make "synthetic products", as defined above. A synthetic product can be a polymer, for example, a peptide, a nucleic acid, a polyester, and the like; or the synthetic product can be a small molecule, preferably of molecular weight less than 1000 a.m.u. Exemplary small molecules which can be synthesized according to the invention include pharmaceuticals such as antibiotics, anxiolytics, steroids, antiinflammatories, analgesics, anticoagulants, antihypertensives, and the like; agricultural chemicals such as herbicides, pesticides, plant growth regulators, and the like; and other chemical compounds which will be apparent to one of skill in the art.

In preferred embodiments, at least one of the substrate compound and the synthetic product has a molecular weight less than 5000 a.m.u., more preferably less than 1000 a.m.u., and still more preferably less than 500 a.m.u. In preferred embodiments, neither the substrate compound nor the synthetic product comprises a peptide. In preferred embodiments, at least one of the substrate compound and the synthetic product is insoluble in water. In preferred embodiments, the substrate compound is soluble in an organic solvent such as THF or acetonitrile.

Examples 8–10 describe the synthesis of the synthetic product 2-(phenylthio)acetic acid.

Solid supports

The invention features the use of solid supports to bind to, or associate with, substrate compounds. A solid support suitable for use in the invention can be chosen by the skilled artisan according to several criteria. In general, a solid support will have one or more of the following properties: 1) It will bind to a substrate compound when the substrate compound is in an associating charge state; 2) It will not substantially bind to a substrate compound when the substrate compound is in a non-associating charge state; 3) It will not react with the substrate compound to form or break any covalent bond; 4) It will not be soluble in the reaction mixture; and 5) It will be separable from the reaction mixture.

Solid supports that satisfy the above criteria can be chosen for each substrate compound and will vary according to the substrate compound structure and charge state. Routine experimentation may be necessary to determine the preferred solid support for a given substrate compound.

A solid support can bind to a substrate compound in an associating charge state through any of several mechanisms, for example, ionic (electrostatic) interactions; hydrophobic interactions; polar interactions, and the like. In preferred embodiments, the solid support does not covalently bind the substrate compound. In preferred embodiments, the solid support has a charge state which is complementary (e.g., of opposite sign) to an associating charge state of the substrate compound. For example, if a substrate compound in an associating charge state has a charge of +1, the solid support preferably has a negative charge.

However, the skilled artisan will appreciate that the solid support is not required to be charged. Thus, a solid support that has no net charge, but is polar, can associate with a charged moiety or substrate compound.

A variety of charged solid supports are known in the art. For example, solid supports that bear a negative charge include, but are not limited to, anionic polymer such as those selected from the group consisting of homo- and co-polymers of styrene sulfonates, alkali metal styrene sulfonates, vinyl sulfonate, acrylamido methyl propane sulfonic acid, acrylates, methacrylates, vinyl acetic acid, crotonic acid, and alkali metal and ammonium salts of copolymers of styrene and substituted styrenes with maleic acid. In an exemplary embodiment, the present method contemplates the use of cation exchange resins such as Amberlite® (a sulfonated polystyrene); IR 120 (a sulfonated polystyrene); polyacrylic acid; and other anionic polymers. Many nonpolymeric supports also bear a negative net charge, including silica, Florisil® (magnesium silicate), and the like.

Likewise, useful cationic polymers for solid suppose which bear a positive charge include, but are not limited to, cationic polymers such as cationic polysaccharide gums, cationic starch, cationic polyvinyl alcohol, cationic polyvinylpyrrolidone, quaternized dextrans, quaternized hydroxy ethyl cellulose, cationic guar gum, glycidyltrimethylammonium chloride ethers of hydroxyethylcellulose, polydimethylenepyrellidinium chlorides, quaternary ammonium derivatives of hydroxy propyl guar, quaternary ammonium salts of hydrolyzed gelatin, and copolymers of dialkylamino alkylmethacrylate. Exemplary cationic supports include 2-(diethylamino)ethyl-Sephadex® (Sephadex-DEAE) and quaternary aminoethyl-Sephadex® (Sephadex-QEA).

Other solid supports which are contemplated for use in the invention include chargeable polymers such as polyacetylene, poly-phenylene, polythienylene and polypyrrole, which can be doped with dopant ions if required. The skilled artisan will be able to select other suitable solid supports.

As mentioned above, a solid support should not substantially bind a substrate compound when the substrate compound is in a non-associating state. The relative binding affinity of a solid support for a substrate compound should be determined for the substrate compound in at least two charge states, for example, a neutral state and a cationic state. Example 4, infra, describes an assay for determining the binding capacity of a solid support for a substrate compound. In preferred embodiments, a solid support will bind no more than 30% as much of a substrate compound when the substrate compound is in a non-associating state as when the substrate compound is in an associating state. For example, if a solid support binds 100 µmol of substrate compound (in an associating state) per gram of solid support, the solid support should bind no more than 30 µmol of substrate compound per gram of solid support when the compound is in a non-associating state. In more preferred embodiments, the solid support binds no more than 20%, still more preferably no more than 10%, and still more preferably no more than 5%, as much of a substrate compound when the substrate compound is in a non-associating state as when the substrate compound is in an associating state.

In another embodiment, a substrate compound binds to, or can become associated with, a solid support when both the substrate compound and the solid support are in an uncharged state. For example, an uncharged substrate compound can become associated with a neutral, uncharged solid support through hydrophobic interactions, van der Waals interactions, polar (but not ionic) interactions, and the like. In an illustrative embodiment, a charged, polar substrate compound, dissolved in a polar liquid phase, does not strongly associate with a nonpolar solid support. Upon redox reaction of a chargeable moiety of the substrate compound, the substrate compound becomes electrically neutral, and the electrically neutral substrate compound becomes associated with the uncharged solid support. Reversal of the redox reaction causes the substrate compound to once again become charged, and to dissociate from the solid support.

Exemplary uncharged solid supports include materials such as polystyrene, polyethylene, polypropylene, polyvinylchloride, and the like.

In certain embodiments, the solid support will not associate with a substrate compound (in a non-associating state) due to a lack of attractive forces. For example, a neutral substrate compound will be less strongly bound to a negatively charged solid support than will a positively charged substrate compound. However, in certain embodiments, a substrate compound in a non-associating charge state will have a charge which is of the same sign as the charge of the solid support, thus leading to electrostatic repulsion between the substrate compound and the solid support. For example, a positively charged substrate compound will, in general, repel a positively charged solid support.

In preferred embodiments, a solid support is easily separable from a reaction mixture. Separation can be achieved in several ways. For example, if the solid support is a particulate material, the reaction mixture can be filtered to remove the solid support. Other separation methods include centrifugation, distillation, and the like. The solid support is preferably not significantly soluble in the reaction mixture.

In another embodiment, the solid support is a solid surface. For example, a solid member made of, or coated with, a suitable material can be introduced into a reaction mixture to associate with a substrate compound. This embodiment is particularly preferred when the charge state of the substrate compound is altered by an electrochemical redox reaction. For example, an electrode, coated wholly or partially with, for example, a sulfonated polystyrene, can be brought into contact with a reaction mixture, and an electrical potential applied to the reaction mixture such that a substrate compound is converted to an associating (in this example, cationic) charge state. The substrate compound then becomes associated with the electrode surface and the electrode is withdrawn from the reaction mixture, thus removing the substrate compound from the reaction mixture.

Although the solid support has been described with respect to solid phases, the invention further contemplates the use of hydrogels and other supports which can be separated from a reaction mixture. Furthermore, the solid support can be soluble under certain conditions and insoluble under other conditions. Thus, a substrate compound can be associated with a soluble support, and the reaction conditions altered (e.g., by lowering the temperature, addition of a nonsolvent, and the like) to cause the support, and the associated substrate compound, to become insoluble and precipitate from solution. The invention also contemplates the use of two immiscible liquid phases, wherein the substrate compound can be made to partition between the two phases by altering the charge state of the substrate compound.

In another embodiment, reactions according to the present invention can be performed by use of a substrate compound that reversibly associates with a solid support, where the solid support includes a selectively chargeable moiety. Thus, a charged substrate compound (comprising, for example, a quaternary amine, or a sulfonate group) can associate with a solid support when a selectively chargeable moiety of the solid support is in an associating charge state, while the charged substrate compound will not associate with the solid support when a selectively chargeable moiety of the solid support is in a non-associating charge state. Also, as described above, the substrate compound can be electrically neutral (uncharged), such that an electrically neutral charge state of the solid support is an associating charge state, and a charge can be conferred on the solid support by suitable manipulation of a selectively chargeable moiety bound to the solid support, to provide a non-associating charge state.

In yet another embodiment of the present invention, a charged substrate compound can associate with a charged solid support, wherein the solid support bears a static charge. For example, a suitably insulated solid surface can hold a static charge, and the charge can be removed by, for example, grounding the solid surface. In this embodiment, a charged substrate compound can be associated with a solid surface when the surface has a static charge, and the substrate compound can be dissociated from the surface by discharging the static charge on the surface. This embodiment is experimentally simple, requiring only a chargeable surface and a source of static electric charge to reversibly associate a substrate compound to a solid surface. No chemical reagents or additional synthetic manipulations are required. Thus, a solid surface could be suitably charged and brought into contact with a solution containing the substrate compound; the substrate compound can become associated with the solid surface, and the solid surface can be removed from the reaction vessel, thereby separating the substrate compound from the reaction mixture.

Reaction mixtures and conditions

The reactions of the present invention may be performed under a wide range of conditions, though it will be understood that the solvents and temperature ranges recited herein are not limitative and only correspond to a preferred mode of the process of the invention.

In general, it is desirable that reactions are run using mild conditions that will not adversely affect a substrate compound, a solid support, reagents, or a synthetic product. For example, the reaction temperature influences the speed of the reaction, as well as the stability of the reactants and catalyst(s), if any. The reactions will usually be run at temperatures in the range of −78° C. to 100° C., more preferably in the range −20° C. to 50° C. and still more preferably in the range −20° C. to 25° C.

In general, the reactions according to the invention will be performed in the liquid phase, e.g., in solution or suspension. The reactions may be run in an inert solvent, preferably one in which the reaction ingredients, excepting the solid support, are substantially soluble. Suitable solvents include ethers such as diethyl ether, 1,2-dimethoxyethane, diglyme, t-butyl methyl ether, tetrahydrofuran (THF) and the like; halogenated solvents such as chloroform, dichloromethane, dichloroethane, chlorobenzene, and the like; aliphatic or aromatic hydrocarbon solvents such as benzene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents. Furthermore, in certain embodiments it may be advantageous to employ a solvent that is not inert to the substrate under the conditions employed, e.g., use of ethanol as a solvent when ethanol is a desired reactant. In embodiments where water or hydroxide are not preferred reactants, the reactions can be conducted under anhydroUs conditions. In certain embodiments, ethereal solvents are preferred.

In certain embodiments it is preferable to perform the reactions under an inert atmosphere of a gas such as nitrogen or argon.

Methods

In one embodiment, the methods of the invention are useful in synthesis of chemical compounds. In this embodiment, the substrate compound acts as a "scaffold" upon which a chemical compound (e.g., a synthetic product) can be synthesized. A reactive moiety is generally selected to be a linker or "handle" between the chargeable moiety and the compound which is synthesized. The selectively chargeable moiety can be in an associating charge state that can associate with a solid support, and a non-associating charge state that does not associate with a solid support. Thus, in an exemplary embodiment, with the substrate compound in a reaction mixture, e.g., in solution, the reactive moiety can be selectively functionalized. When reaction is complete, the chargeable moiety is converted to an associating charge state (if it was not already in such a charge state) and associated with a solid support (e.g., by addition of the solid support to the reaction mixture). The solid support can then be separated from the reaction mixture, e.g., by filtration, thereby removing, or reducing the amount of, impurities such as excess or spent reagents. The solid support with the associated substrate compound can optionally be washed or further purified to remove undesired components. The substrate compound can be released from the solid support by conversion to a non-associating charge state and dissociation from the solid support into a reaction mixture.

The invention thus provides methods of synthesis that have many of the advantages associated with solid phase synthesis (SPS), while avoiding some of the potential drawbacks of conventional SPS. For example, as with conventional SPS, purification of the desired product is simple and rapid. However, in conventional SPS, reactions occur on solid supports, which can lead to problems such as difficulties with solvation, anomalous reaction kinetics, inability to effectively use insoluble catalysts or reagents, and the like. In contrast, the methods of the invention feature reactions in the liquid phase, followed by purification in the solid phase.

The present invention also provides methods for combinatorial synthesis. The synthesis of combinatorial libraries is well known in the an and has been reviewed (see, e.g., E. M. Gordon et al., *J. Med Chem.* 37:1385–1401 (1994)). Such libraries can be synthesized according to a variety of methods. For example, a "diversomer library" can be created by the method of Hobbs DeWitt et al. (*Proc. Natl. Acad Sci. U.S.A.* 90:6909 (1993)), using the sequestration techniques of the present invention in place of conventional resin supports. Aliquots of substrate compound are placed in an array of reaction vessels, and one of a plurality of reactants is introduced into each vessel. After reaction, the modified substrate compounds are selectively charged (if needed) to an associating charge state, and the substrate compounds are associated with a solid support, and washed if desired. Aliquots of solid supported substrate compound can be divided, if desired, into further reaction vessels. The substrate compound in each vessel can then be convened to a non-associating charge state, and the substrate compound solubilized; further cycles of reaction, association with a solid support, and purification can take place to yield a library of compounds.

Other synthesis methods, including the "tea-bag" technique of Houghten (see, e.g., Houghten et al., *Nature* 354:84–86 (1991)) can also be used to synthesize libraries of compounds according to the subject invention.

Combinatorial libraries can be screened to determine whether any members of the library have a desired activity, and, if so, to identify the active species. Methods of screening combinatorial libraries have been described (see, e.g., Gordon et al., *J Med Chem.*, op. cit.). Soluble compound libraries can be screened by affinity chromatography with an appropriate receptor to isolate ligands for the receptor, followed by identification of the isolated ligands by conventional techniques (e.g., mass spectrometry, NMR, and the like). Immobilized compounds can be screened by contacting the compounds with a soluble receptor; preferably, the soluble receptor is conjugated to a label (e.g., fluorophores, colorimetric enzymes, radioisotopes, luminescent compounds, and the like) that can be detected to indicate ligand binding. Alternatively, immobilized compounds can be selectively released and allowed to diffuse through a membrane to interact with a receptor.

Combinatorial libraries of compounds can also be synthesized with "tags" to encode the identity of each member of the library (see; e.g., W. C. Still et al., PCT Publication No. WO 94/08051). In general, this method features the use of inert, but readily detectable, tags, that are attached to the substrate compound. When an active compound is detected (e.g., by one of the screening techniques described above), the identity of the compound is determined by identification of the unique accompanying tag. This tagging method permits the synthesis of large libraries of compounds which can be identified at very low levels.

In preferred embodiments, the libraries of compounds synthesized according to the present invention contain at least 30 compounds, more preferably at least 100 compounds, and still more preferably at least 500 compounds. In preferred embodiments, the libraries contain fewer than $10^9$ compounds, more preferably fewer than $10^8$ compounds, and still more preferably fewer than $10^7$ compounds.

Apparatus

The methods of the invention can be performed with automated synthesis apparatus. Accordingly, in another aspect, the invention includes an apparatus for use in an automated chemical reaction process which employs the subject reversible sequestration method. Typical instrumentation includes one or more reaction vessels for maintaining a solution phase reaction mixture containing a substrate compound having a chargeable moiety as described above. Suitable reaction vessels are formed from material amenable to the reaction conditions intended to be carried out therein, e.g., are selected on the basis of chemical compatibility, and include glass or polymers (e.g., polypropylene or polyethylene) as appropriate. In most embodiments, the portion of the reaction vessel in contact with the reaction mixture will typically be made of material which does not substantially sequester the chargeable moiety in any of its charge states that the moiety will attain in the subject process. However, it will be apparent that, in other embodiments, all or a portion of the reaction vessel walls contacting the reaction mixture can be formulated to provide the solid support that sequesters one of the charge states of the chargeable moiety. For example, the reaction vessel can be formed with a polymer including a charged group, e.g., a sulfonated polystyrene, which will sequester the chargeable moiety in one of its oxidation states.

The reaction vessel can be designed to be sealable such that the vessel may be both pressurized (or depressurized) and/or tipped, rocked and/or vortexed without loss or spillage of reaction mixture contained therein. The compatibility of the reaction vessel with pressurization may accordingly be important to the selection of the vessel material and physical dimensions.

The reaction vessel can be configured to facilitate single flow-path loading and evacuation, e.g., the reaction vessel can include two ports proximal to opposite ends of the vessel. However, it will also be apparent that other embodiments of the reaction vessel can provide for aspiration of reaction mixture using the same port(s) as reagent/solvent addition occurs through.

In preferred embodiments, the apparatus is configured for multiple simultaneous synthesis and a plurality of reaction vessels are provided, preferably in the form of arrays of reaction vessels, such as microtitre plate-type or other similar formats amenable to automation.

The apparatus also provides one or more reagent vessels, and a delivery system for delivering reagents from the reagent vessels to the reaction vessels. In general, the reagent vessels are provided as reservoirs of reagents used to generate reaction mixtures in the reaction vessel(s). This includes reagents used in the desired synthetic reaction, as well as solvents for washing, for example, the solid support, the reaction vessels, and transfer lines.

The delivery system includes the transfer lines from the reagent vessels to the reaction vessels, as well as any accompanying valves and pumping means. The delivery system may also (optionally) include lines, pumps and valves for removing the reaction mixture from the reaction vessel(s). The delivery system can also include transfer lines for conducting gases. Suitable reagent vessels are selected on the basis of solvent compatibility. Suitable transfer lines and valves are selected by similar criteria, as well as volume and flow-rate requirements, flexibility, durability, etc. Preferred materials include teflon, polyethylene and polypropylene.

The apparatus further provides a solid support for reversibly sequestering the chargeable moiety from the reaction mixture in an oxidation-dependent manner. Exemplary solid supports can be provided, as described above, in any form suitable for disposition in the reaction mixture of the reaction vessel. Exemplary solid supports include: beads or other insoluble particles; a coating or sheath of an electrode; or as a portion of the reaction vessel wall.

Still another component of the apparatus is the redox means which provide for reversible oxidation and reduction of the chargeable moiety between a charge state which associates with the solid support and a charge state which does not readily associate with the solid support. As set out above, the oxidation/reduction of the chargeable moiety can be provided by, for example, chemical oxidants or reductants, electrochemical reactions, electromagnetic radiation (e.g., photooxidation or reduction), and combinations thereof. Accordingly, in illustrative embodiments, the redox means may by any combination of: reagents for oxidizing or reducing the chargeable moiety; a source of electric current, e.g., an electrode, for electrochemically oxidizing or reducing the chargeable moiety; and/or a light source (coherent or non-coherent) for photooxidizing or photoreducing the chargeable moiety.

In preferred embodiments, a microprocessor is included for coordinating operation of one or more of the delivery system, solid support means and redox means.

Figure 1:
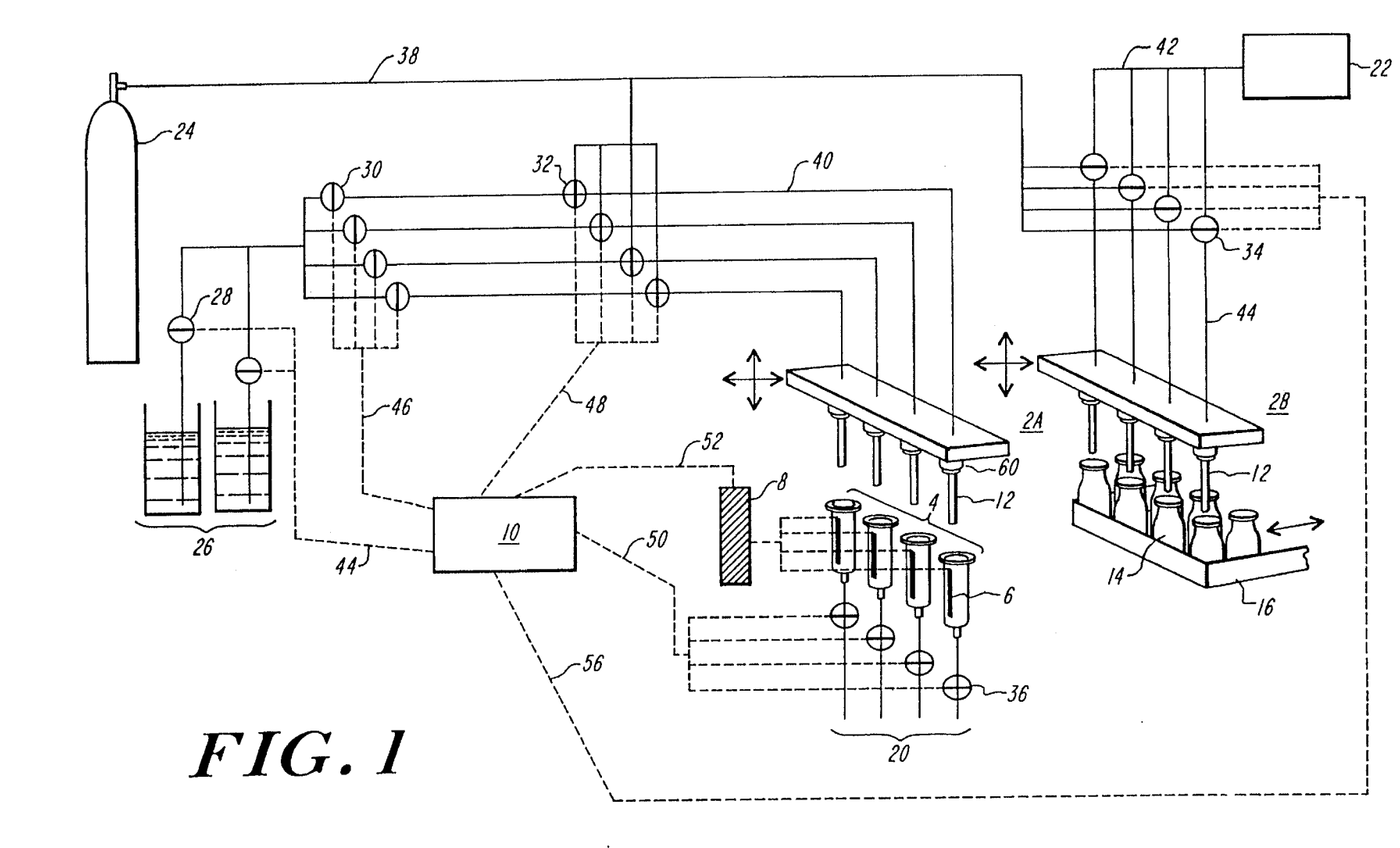
FIG. 1 depicts an apparatus for providing reversible solid phase sequestration of solution phase reaction components.

The system used for carrying out chemical reactions including the subject reversible solid phase sequestration of solution phase reaction components can have one of several forms. FIG. 1 is a schematic diagram of one illustrative embodiment of the subject synthesizer and is configured for simultaneous multiple chemical synthesis. Reaction vessels 4 are disposable reaction vessels having a filter in the bottom portion thereof, wherein a solidphase resin support is packed. The resin is, for example, Florisil, and the filter has a mesh size smaller than the particle size of the resin. Valves 36 also serve to control outflow of fluid from the bottom of each reaction vessel 4. In one embodiment, electrode(s) 6 are disposed in the reaction vessel 4 where electrochemical oxidation or reduction is desired as part of the subject process.

The exemplary apparatus further comprises two (or more) modules 2A and 2B, which are provided for articulation with the reaction vessels 4. Each member holds needles 12, and can be moved horizontally and vertically by, for example, articulation with robotic arms. The needles can be seated in the reaction vessels 4 and the vessels sealed by gaskets 60. As illustrated, needles 12 of module 2A are connected by transfer lines 40 with a series of reagent vessels 26, and gas source 24. Valves/pumps 28, 30 and 32 selectively control flow of fluids from the reagent vessels 26 and gas source 24 to the needles 12. In operation, the multiple reagent vessels 26 preferably, though optionally, contain reagents which are common to reaction mixtures to be provide in each of the reaction vessels 4. For example, such reagents include solvents, buffers, acids, bases, washes and the like, as well as reagents for chemically oxidizing or reducing the chargeable moiety. Gases can be provided for pressurizing the reaction vessels 4, as well as for bubbling through reaction mixtures in the reaction vessels 4 and for purging the transfer lines 40 and needles 12.

Module 2B can also be moved horizontally and vertically to articulate with reaction vessels 4 as well as reagent vessels 14. Needles 12 of module 2B are connected by transfer lines 44 with gas source 24 and vacuum source 22. Valves 34 selectively control flow of gases between transfer lines 44 and gas source 24 and vacuum source 22. In operation, valves 34 can be used to provide a fluid connection between vacuum lines 42 and transfer lines 44 to provide a aspirating vacuum at the tips of needles 12 to remove a volume of fluid from reaction vessels 14. Likewise, valves 34 can be used to provide a fluid connection between pressure lines 38 and transfer lines 44 to provide a purging pressure in transfer lines 44 and needles 12. In such a manner, alternating between vacuum and pressure sources and dead pressure (valve closed to both sources), fluid can be aspirated from reagent vessels 14 and transferred to reaction vessels 4. In operation, the multiple reagent vessels 14 preferably, though optionally, each individually contain reagents which are unique to a reaction mixture to be carried out in a discrete reaction vessel. For convenience, such reagent vessels 14 may be provided in an array 16 which can be, for example, carousel or rack systems as known in the art.

The exemplary instrument is further described by way of illustrating its use. In one node of operation, the apparatus is configured with reaction vessels 4 containing a solid support therein. Valves 36 are in a position which prevents fluid flow out of the bottom of the vessel. The reaction vessels 4 are charged with common reagents for the first reaction of the intended synthesis. Such reagents can be provided by hand, or preferably, transferred from reagent vessels 26 by transfer lines 40. Reagents which are unique for a reaction to be carried out in only a subset of the reaction vessels 4 can be transferred from reagent vessels 14 by module 2B.

After certain reaction steps, it will be desirable to immobilize the product of that step to the solid support. Accordingly, an oxidant (or reductant as needed), can be added to the reaction mixture from reagent vessels 26. After a time appropriate for conversion of the chargeable moiety to a charge state which is sequestered by the solid support, and time sufficient for an adequate proportion of those chargeable moieties to become sequestered, valves 36 can be opened to remove the unsequestered components of the reaction mixture through transfer lines 20. To facilitate purging of the reaction vessels 4, the vessels can be pressurized by opening valves 32 when needles 12 of module 2A are articulated with reaction vessels 4. Subsequent to purging the reaction vessels 4, the solid support can be washed (optional), valves 36 returned to a closed position, and the reaction vessels 4 recharged with at least one reagent for the next synthesis reaction, as well as a reductant (or oxidant as needed) for changing the charge state of the chargeable moiety to one which is not sequestered by the solid support, e.g., the sequestered product from the previous round of synthesis is released back into solution for reaction in the next round.

When the final product(s) are produced in this automated reaction scheme, the products can be removed from the reaction vessels 4 by, for example, transfer lines 20 or aspirated by needles 12.

All of the steps are accomplished by the opening and closing of individual valves that are, preferably, controlled by a microprocessor 10, such as may be provided in the form of a personal computer and system software that allow the user to do these steps individually or in any combination and length. In the illustrative embodiment, control lines 44, 46, 50 and 56 can (i) activate the valve and/or pump structures to transfer solutions from the reagent vessels 26 to reaction vessels 4; (ii) activate the valve structure to communicate the compressed gas source 24 with the transfer lines 40 and, if desired, with reaction vessels 4; (iii) activate the valve structures to communicate one of either the vacuum source 22 or compressed gas source 24 with transfer lines 44 to transfer solution from reagent vessels 14 to the reaction vessels 4; (iv) activate the valve structures to communicate the reaction vessels 4 with transfer lines 20 to remove solutions from the reaction vessels. When the apparatus includes one or more electrodes 6 for electrochemical oxidation or reduction, the microprocessor 10 can be used to control the electrode power supply 8, such as by control lines 52.

A variety of valves can be used and actuated in a variety of ways compatible with the selected chemistry. In a preferred embodiment, teflon diaphragm valves are actuated pneumatically or by solenoid.

In other preferred embodiment, the apparatus can include: heating and/or cooling baths or sleeve for any of the reaction vessels 4, or reagent vessels 26 or 14; optical, acoustical and floating sensors or the like for detecting fluid presence or fluid flow in any of the transfer lines or vessels; vortexing or rocking means for facilitating mixing in the reaction vessels.

Moreover, it will be appreciated that the valve configuration described above can be substituted with a smaller number of valves, such as a single valve structure to control all transfer lines from a reagent vessel 26 or compressed gas source 24. Likewise, the vacuum source/compressed gas combination for transfer of reagents between reagent vessels 14 and the reaction vessels can be replaced by mechanical pumps or, more preferably, automated multichannel pipettes. Alternatively, the subsystem, along with module 2B, can be integrated as part of the module 2A subsystem.

In still other embodiments, the solid support and electrode (if employed) can be provided as parts of a separately disposable element, e.g., part of a module subsystem similar to module 2A. In this embodiment, which is particularly useful when the reaction vessels are in the form of microtitre plates or the like, the module subsystem including the solid support can be articulated with the reaction vessel at a time when sequestration of the chargeable moiety/reaction product is desired, and removed after the chargeable moiety has been released back into solution. To further illustrate, where such an embodiment of the solid support is provided with a microtitre plate array of reaction vessels, the module can be articulated with the reaction vessels to dispose the solid support in the reaction mixture, chargeable moieties sequestered to the solid support, the solid support withdrawn from the reaction vessels, washed, and redisposed in the reaction vessels of a new microtitre plate where the chargeable moiety is released and the next round of synthesis is carried out.

The combination of reagent transfer, reagent measurement, reagent combining and redox reactions described above does not limit the user to choice of synthesis strategies and allows an extremely wide range of synthesis schemes. This combination is amenable to scale up, allowing the subject method and apparatus to be used on a manufacturing scale.

Exemplification

In the Examples described below, thin-layer chromatography (TLC) was performed on silica gel plates eluted with 50/50 ethyl acetate/hexane as eluent. The reaction products were visualized by oxidation with DDQ in ether, which was applied with a cotton swab.

| compound | rf | color of oxidized compound |
|---|---|---|
| nitro (I) | 0.78 | green |
| amino (II) | 0.50 | purple |
| 2-chloroethyl carbamate (III) | 0.65 | green |
| oxazolidinone (IV) | 0.31 | green |

EXAMPLE 1

Synthesis of 4',4"-[4-nitrobenzylidine]bis[N,N-dimethylaniline](I)

N,N-dimethylaniline (75 mL), 4-nitrobenzaldehyde (30 g, 0.2 mmoles) and zinc chloride (30 g) were combined in a 500 mL round bottom flask. The flask was placed in an oil bath set at 110° C. and the contents were stirred by use of a magnetic stir bar. The heating was continued for one hour after which water (250 mL) was added. The flask was fitted with a condenser arranged for distillation and the mixture was heated to reflux. Distillation was continued until the distillates contained little N,N-dimethylaniline (about 200 mL of distillate was collected). Water was added occasionally throughout the distillation to maintain a volume in the flask of approximately 200 mL. After cooling, the solid yellow product was isolated by filtration and washed well with water. The solid product was air dried and then recrystallized from 400 mL of 2-ethoxyethoxyethanol. The purified product was isolated by filtration and washed with diethyl ether. After air drying there was obtained 61.3 g (82%) of product as a golden yellow solid melting at 179°–180° C.

EXAMPLE 2

Synthesis of 4',4"-[4'"-(3-oxazolidin-2-one)benzylidine]bis]N,N-dimethylaniline](II)

bubbler. Nitrogen flow was started and the flask was purged with dry nitrogen. Dry THF (100 mL) was introduced by syringe and the stirring was commenced. After complete dissolution of the nitro compound, one of the septa was removed and 10% Pd on carbon catalyst (1.0 g) was introduced. The septum was replaced and the flask was purged with nitrogen for 10 minutes. The nitrogen flow was stopped and hydrogen was introduced into the flask through a line connected to a syringe needle inserted through a septum. The flow rate was adjusted to produce bubbles in the bubbler at about two bubbles per second. Stirring and hydrogen introduction was continued for two hours during which time the yellow color of the nitro compound faded to provide a clear solution. The hydrogen flow was stopped and the flask was purged with nitrogen. An aliquot of the reaction mixture was taken and examined by TLC and it was shown that the starting nitro compound had been cleanly converted to the amino compound. With the nitrogen flow continuing at about two bubbles per second, the flask was cooled in an ice bath after which 2-chloroethyl chloroformate (3.8 g, 2.9 mL, 26.6 mmoles) was slowly added by syringe with stirring. After stirring on ice for one hour, an aliquot of the slurry was examined by TLC and it was shown that the amine had been cleanly converted to the 2-chloroethyl carbamate (III). While still under nitrogen, the slurry was cooled in an

A three neck, round bottom flask was charged with 10 g (26.6 mmoles) of the nitro compound (4',4"-[4-nitrobenzylidine]bis[N,N-dimethylaniline]; see Example 1) and a stir bar and was sealed with septa on each of the three necks. A nitrogen line was connected to the flask via a syringe needle inserted through one of the septa. A line connected to a second septum via a syringe needle led to an oil-filled acetone-dry ice bath and lithium bis(trimethylsilyl)amide (1.0M in THF, 53.2 mL, 53.2 mmoles) was introduced by syringe with stirring. The dry ice bath was removed and the reaction mixture was stirred at room temperature overnight. The reaction mixture was then poured into a separatory funnel containing 400 mL of water and 400 mL of diethyl ether. After shaking, the aqueous phase was settled, withdrawn along with the spent catalyst and discarded. The ether solution was washed once with 200 mL of water, dried over magnesium sulfate and quickly filtered to prevent crystallization of the product. TLC of the pale yellow ether solution showed one major product spot. The ether was stripped under vacuum and the residue was quickly dissolved in 50 mL of hot ethyl acetate. Upon cooling to room temperature, the oxazolidinone (IV) crystallized as a white powder. This was isolated by filtration, washed with ethyl acetate and air dried. Yield of product was 7.5 g, or 68%, based on starting nitro compound. The melting point was 176°–177° C.

EXAMPLE 3

Synthesis of
4',4"-[4-N-methyl-N-hydroxyethylaminobenzyl-idine]bis[N,N-dimethylaniline]

A solution of the oxazolidinone (1.0 g, 2.24 mmoles) in 20 mL of dry THF was prepared under nitrogen. A stir bar was placed in the solution and stirring was commenced. To the stirred solution borane-methylsulfide (1.06 mL, 0.85 g, 11.0 mmoles) was added. The clear solution was then refluxed under nitrogen with stirring for 24 hours. A solution of 2.0 mL of conc. HCl diluted to 20 mL in water was cautiously added to prevent excessive frothing from hydrogen evolution and refluxing under nitrogen was continued for another 30 minutes. The reaction mixture was transferred to a separatory funnel and diluted with 100 mL of diethyl ether. The mixture was basified by addition of conc. NH$_4$OH and extracted twice with 50 mL portions of water. The ether layer was dried over magnesium sulfate, filtered and evaporated under vacuum. The residue was chromatographed on silica using 1% methanol in dichloromethane as eluent. After elution of a small amount of unchanged starting material, the product was isolated as several fractions that were pooled and evaporated under vacuum. In this manner 0.5 g (51%) of the desired product were obtained.

EXAMPLE 4

Determination of Dye Capacity for Several Solid Supports

Dye capacity for solid supports were determined by stirring weighed portions of the supports in measured portions of a stock acetonitrile solution of crystal violet of known concentration for 15 hours. The supports were allowed to settle and the supernatant was examined by visible spectroscopy. By comparison of the absorbance of the supernatant to the absorbance of the stock dye solution the amount of dye adsorbed to the support could be determined.

Stock Solution: $1.01 \times 10^{-4}$M, e=98,713

| Support | Weight | Dye adsorbed (moles) | Capacity (mole/g) |
|---|---|---|---|
| Amberlite 15 | 1.153 g | $9.3 \times 10^{-7}$ | $8.1 \times 10^{-7}$ |
| Amberlite DP1 | 1.474 g | $6.6 \times 10^{-7}$ | $4.5 \times 10^{-7}$ |
| IR 120 | 0.955 g | $5.9 \times 10^{-7}$ | $6.2 \times 10^{-7}$ |
| silica | 0.500 g | $9.1 \times 10^{-7}$ | $1.8 \times 10^{-6}$ |
| Florisil | 0.137 g | $9.36 \times 10^{-7}$ | $6.8 \times 10^{-6}$ |

To demonstrate that the dye could be removed from the support by reduction to the leuco form, a portion of dyed Florisil was prepared and after the loading was determined as described above, the solid was separated from the supernatant dye solution and was washed twice in 10 mL portions of acetonitrile by decantation. After the second decantation, the solid was suspended in 10 mL of acetonitrile and was treated with 2 mg of sodium cyanoborohydride. Brief warming with agitation at 50° C. caused the blue color of the dyed Florisil to turn colorless. After the solid was settled, a portion of the colorless supernatant was removed and treated with three drops of acetic acid and 10 mg of the oxidant dichlorodicyanoquinone (DDQ). By comparison of the absorbance of the oxidized, blue solution to the absorbance of the stock dye solution the amount of dye released from the Florisil could be determined.

| Support | Weight | Dye adsorbed (moles) (initial loading) | Dye released (mole) (after oxidation) | % released |
|---|---|---|---|---|
| Florisil | 0.122 g | $9.51 \times 10^{-7}$ | $5.65 \times 10^{-5}$ | 62.3% |

EXAMPLE 5

Synthesis of
N,N-bis-(2'-chloroethyl)-4-aminobenzaldehyde

A one liter, three-necked, round bottom flask equipped with an overhead stirrer, thermometer and dropping funnel was charged with 264 g (3.61 moles) of dry dimethyl formamide. The flask was immersed in an ice bath, the stirring was commenced, and when the internal temperature reached 10° C. phosphorous oxychloride (151.8 g, 92.3 mL, 0.990 moles) was added via the dropping funnel at a rate that kept the temperature below 15° C. (about one hour). After addition of the phosphorous oxychloride, the pale yellow solution was stirred on ice for ten minutes after which a solution of N-phenyldiethanolamine (59.8 g, 0.33 mmoles) dissolved in 50 mL of dimethylformamide was added through the dropping funnel at a rate that kept the temperature below 20° C. (about 0.5 hours). Upon complete addition of the N-phenyldiethanolamine, the ice bath was removed, the thermometer was replaced with a condenser and the solution was heated in an oil bath at 100° C. for two hours. After cooling to about 40° C., the warm orange solution was poured onto 1 kg of ice with stirring. The pH of the resulting solution was adjusted to 6.0 by addition of 800 mL of an aqueous solution containing 500 g of potassium acetate which caused the product to crystallize. The slurry was kept at $0^\delta$ C. in a refrigerator overnight and the product was isolated by filtration on a Buchner funnel. The pale yellow solid was washed with two 300 mL portions of water and sucked as dry as possible on the funnel. After air drying for four hours, the solid was dissolved in 250 mL of boiling 2-propanol. The hot solution was first filtered through a fluted filter paper and then cooled on ice which caused the product to precipitate as a white solid. This was isolated by filtration washed with two 100 mL portions of 2-propanol and then air dried. The yield of the product as a white solid was 63 g (78%) melting at 86°–87° C.

EXAMPLE 6

Synthesis of 4,4',4''-methylidynetris(N,N-bis-2-chloroethylaniline)

N-phenyldiethanolamine (36.1 g, 0.20 moles), N,N-bis(2'-chloroethyl)-4-aminobenzaldehyde (24.6 g, 0.10 moles) and zinc chloride (15 g) are combined in a 500 mL round bottom flask. The flask is placed in an oil bath set at 110° C. and the contents are stirred by use of a magnetic stir bar. The heating is continued for one hour after which conc. HCl (86.4 mL; 1.0 moles) and an additional 136.3 g (1.0 moles) of zinc chloride are added. The flask is fitted with a condenser and the mixture is heated at 150° C. for one hour. After cooling to about 50° C., water (500 mL) is added followed by a solution of sodium acetate (250 g) dissolved in 200 mL of water. After cooling, the solid product is isolated by filtration and washed with water. The title product is air dried and then recrystallized. The purified product is isolated by filtration, washed with diethyl ether, and air dried.

EXAMPLE 7

Synthesis of a Crystal Violet Dendrimer

27
-continued

Diethanolamine (105 g, 1.0 moles) and 4,4',4"-methylidynetris (N,N-bis-2-chloroethylaniline) (6.64 g, 10 mmoles) are combined in a round bottom flask and are heated with stirring at 150° C. under nitrogen for two hours. The flask is then arranged for vacuum distillation and the excess diethanolamine is removed by vacuum distillation. After cooling, the residue is recrystallized to provide the title product.

EXAMPLE 8

Preparation of 2-(Phenylthio)acetic acid Using Dye Sequestration

28
-continued

A 100 mL round bottom flask containing a magnetic stir bar was charged with 46.5 mg (0.107 mmoles) of 4',4"-[4-N-methyl-N-hydroxyethylaminobenzylidine]bis[N,N-dimethylaniline] (synthesized in Example 3) and 50 mL of dry acetonitrile. The flask was sealed with a septum and connected to a nitrogen source and bubbler through the use of syringe needles. The flask was purged with nitrogen and cooled in an ice bath. With stirring, triethylamine (0.101 g, 0.139 mL, 1.0 mmoles) was added followed by the dropwise addition of chloroacetyl chloride (0.113 g, 0.078 mL, 1.0 mmoles). After stirring on ice for three hours, TLC (silica, 50/50 ethyl acetate/hexane) showed complete conversion of the starting material to a single new product. The solution was treated with a 0.514M solution of o-chloranil (1.2 mL, 0.62 mmoles) and acetic acid (0.2 mL), causing the formation of an intense blue indicating the formation of the cationic dye. After stirring for one hour, Florisil (15 g) was added and the mixture was stirred for five minutes by which point most of the dye had been adsorbed on the Florisil. The dark blue solid was isolated by filtration and washed with four portions (20 mL each) of acetonitrile. The damp solid is resuspended in 40 mL of dry acetonitrile for use in the next step (Example 9).

EXAMPLE 9

Preparation of 2-(Phenylthio)acetic acid Using Dye Sequestration

The dyed Florisil, from Example 8, was suspended in 40 mL of dry acetonitrile under nitrogen and was agitated as a 1.03M solution of sodium cyanoborohydride in dry THF is added (0.66 mL, 0.68 mmoles). The mixture was warmed to 40° C. with agitation and then stirred overnight at room temperature. At this point, the Florisil was removed by filtration and the solid was washed with dry acetonitrile. TLC (silica, 50/50 ethyl acetate/hexane) showed clean conversion to a new product spot with a small amount of unreacted starting alcohol. The combined organic solution (52 mL) was transferred to a 100 mL round bottom flask equipped with a stir bar and sealed with a septum. After purging with nitrogen, the stirred solution was treated with thiophenol (0.044 g, 0.041 mL, 0.4 mmoles) and lithium bis(trimethylsilyl)amide (1.0M, 0.20 mL, 0.2 mmoles). The mixture was stirred overnight at room temperature. The clear solution was treated with a 1.0M solution of dichlorodicyanoquinone in THF (DDQ, 2.5 mL, 2.5 mmoles) causing the immediate formation of an intense blue indicating the formation of the cationic dye. Florisil (15 g) was added and the mixture was stirred for five minutes, by which time all of the dye had been adsorbed onto the Florisil. The dark blue solid was isolated by filtration and washed with four portions (20 mL each) of acetonitrile, at which point the filtrates were colorless. A second wash of 20% methanol in methyl acetate flushed excess acetonitrile from the solid. The damp solid was carried on for use in the next step (Example 10).

EXAMPLE 10

Preparation of 2-(Phenylthio)acetic acid Using Dye Sequestration

The dyed Florisil, from Example 9, is suspended in 100 mL of 20% methanol in methyl acetate containing 2 mL of acetyl chloride per 100 mL of solvent mixture (equivalent to 0.28M HCl in 20% methanol/methyl acetate). The blue color of the Florisil immediately turned green as the dye became protonated. The Florisil slurry was stirred at room temperature for three days. At this point, the Florisil was removed by filtration and the solid was washed with three portions (10 mL each) of 20% methanol in methyl acetate. The combined organic filtrates were stripped under vacuum to a volume of 8 mL. The concentrated solution was analyzed by HPLC. By comparison to standards, it was determined that the product was a mixture of thiophenoxyacetic acid and the methyl ester (methyl thiophenoxyacetate).

The yield of thiophenoxyacetic acid was $2.83 \times 10^{-5}$ mol, and the yield of methyl thiophenoxyacetate was $1.08 \times 10^{-5}$ mol. Thus, the combined product yield was $3.91 \times 10^{-5}$ mol, representing an overall yield of 36.6% based on the amount of dye used (Example 8).

The cationic dye can be recovered from the solid support and reused for another synthesis.

Those skilled in the art will recognize, or be able to ascertain using no more than routine experimentation, numerous equivalents to the specific procedures described herein. Such equivalents are considered to be within the scope of this invention and are covered by the following claims.

The contents of all references described herein are hereby incorporated by reference.

Other embodiments are within the following claims.

What is claimed is:

1. A method for modifying a substrate compound, the method comprising:
   (i) providing, in a reaction mixture, a substrate compound comprising a reactive moiety;
   (ii) contacting the reactive moiety with a reactant to form a modified substrate compound;
   (iii) providing a solid support, wherein one of said substrate compound and said solid support comprises a selectively chargeable moiety (SCM) having a non-associating charge state;
   (iv) altering the non-associating charge state of the selectively chargeable moiety to an associating charge state;
   (v) contacting the modified substrate compound with the solid support such that the modified substrate compound is sequestered by the solid support; and
   (vi) altering the associating charge state of the selectively chargeable moiety to a non-associating charge state such that the modified substrate compound is not sequestered by the solid support.

2. The method of claim 1, wherein the substrate compound comprises a selectively chargeable moiety.

3. The method of claim 2, wherein the substrate compound has a molecular weight less than about 5000 a.m.u.

4. The method of claim 3, wherein the substrate compound has a molecular weight less than about 1000 a.m.u.

5. The method of claim 3, wherein the substrate compound has a molecular weight less than about 500 a.m.u.

6. The method of claim 2, wherein the substrate compound is insoluble in aqueous solution.

7. The method of claim 2, wherein the substrate compound comprises at least two selectively chargeable moieties.

8. The method of claim 7, wherein the at least two selectively chargeable moieties are different chargeable moieties.

9. The method of claim 1, wherein the solid support comprises a selectively chargeable moiety.

10. The method of claim 1, wherein at least one of an oxidizing or reducing step for reversibly oxidizing the SCM comprises a chemical redox reaction.

11. The method of claim 1, wherein at least one of an oxidizing or reducing step for reversibly oxidizing the SCM comprises an electrochemical redox reaction.

12. The method of claim 1, wherein at least one of an oxidizing or reducing step for reversibly oxiding the SCM comprises photochemical redox reaction.

13. The method of claim 1, wherein the solid support is insoluble.

14. The method of claim 13, wherein the solid support comprises an electrode including an adsorbent which associates with an SCM in an associating charge state and associates less with an SCM in a non-associating charge state.

15. The method of claim 13, wherein the solid support is selectively chargeable.

16. The method of claim 1, wherein the SCM comprises a reversibly oxidizable dye group.

17. The method of claim 16, wherein the dye is a cationic dye or an anionic dye.

18. The method of claim 16, wherein the dye is selected from the group consisting of xanthenes, acridines, phenazines, azines, oxazines, thiazines, cyanines, methines, polymethines, viologens, quinones, diphenylmethanes, triarylmethanes, and azuleniums.

19. A method for reversibly associating a compound with a solid support, the method comprising:
   (i) providing, in a reaction mixture, a compound including a selectively chargeable moiety (SCM) which can be reversibly oxidized between an associating charge state which can associate with the solid support and a non-associating charge state which associates less with the solid support;
   (ii) contacting the reaction mixture containing the compound with a solid support under conditions that the SCM is in the associating charge state and the compound associates with the solid support;
   (iii) separating the solid support from at least a portion of the mixture; and
   (iv) altering the charge state of the SCM to a non-associating charge state such that the compound dissociates from the solid support.

20. A method for modifying a substrate compound, the method comprising:
   (i) providing, in a reaction mixture, a substrate compound comprising a selectively chargeable moiety having a non-associating charge state, and a reactive moiety;
   (ii) contacting the reactive moiety with a reactant to form a modified substrate compound;

(iii) altering, by an electrochemical redox reaction, the non-associating charge state the selectively chargeable moiety to an associating charge state;

(iv) contacting the selectively chargeable moiety with a solid support such that the modified substrate compound is sequestered by the solid support;

(v) separating the solid support from the at least a portion of the mixture; and (vi) altering, by an electrochemical redox reaction, the associating charge state of the selectively chargeable moiety to a non-associating charge state such that the modified substrate compound is not sequestered by the solid support.

21. A method for reversibly sequestering a substrate compound on a solid support, the method comprising:

(i) providing in a reaction mixture, a substrate compound comprising a selectively chargeable moiety;

(ii) reacting the substrate compound with a reactant;

(iii) contacting the reaction mixture with a means for altering an oxidation state of the chargeable moiety from a state which does not bind to the solid support to a state which does bind to the solid support;

(iv) contacting the substrate compound with the solid support such that the substrate compound becomes sequestered by the support;

(v) disposing the support in a second reaction mixture;

(vi) contacting the reaction mixture with a means for altering an oxidation state of the chargeable moiety from a state which does bind to the solid support to a state which does not bind to the solid support; such that the substrate compound is not sequestered by the support.

22. The method of claim 21, further comprising, after step (iv), the step of washing the solid support. such that the substrate compound is not sequestered by the support.

23. A method for synthesizing a synthetic product, the method comprising:

(i) providing in a reaction mixture, a substrate compound comprising a reactive moiety and a selectively chargeable moiety (SCM) having a non-associating charge state;

(ii) contacting the reactive moiety with a reactant to form a modified substrate compound including a synthetic product;

(iii) altering the non-associating charge state of the selectively chargeable moiety to an associating charge state;

(iv) contacting the modified substrate compound with a solid support such that the modified substrate compound is sequestered by the solid support;

(v) altering the associating charge state of the selectively chargeable moiety to a non-associating charge state such that the modified substrate compound is not sequestered by the solid support; and (vi) cleaving the synthetic product from the substrate compound.

* * * * *